(12) United States Patent
Boucher et al.

(10) Patent No.: US 6,607,544 B1
(45) Date of Patent: *Aug. 19, 2003

(54) EXPANDABLE PREFORMED STRUCTURES FOR DEPLOYMENT IN INTERIOR BODY REGIONS

(75) Inventors: Ryan P Boucher, San Francisco, CA (US); Mark A Reiley, Piedmont, CA (US); Robert M Scribner, Los Altos, CA (US); Karen D Talmadge, Palo Alto, CA (US)

(73) Assignee: Kyphon Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/420,529

(22) Filed: Oct. 19, 1999

Related U.S. Application Data

(63) Continuation-in-part of application No. 09/088,459, filed on Jun. 1, 1998, now abandoned, which is a continuation-in-part of application No. 08/788,786, filed on Jan. 23, 1997, now Pat. No. 6,235,043, which is a continuation of application No. 08/188,224, filed on Jan. 26, 1994, now abandoned.

(51) Int. Cl.[7] .............................................. A61B 17/56
(52) U.S. Cl. ........................ 606/192; 606/53; 604/96.01
(58) Field of Search ................................ 606/60, 61–75, 606/86–89, 190, 191, 192, 194, 53; 604/96.01

(56) References Cited

U.S. PATENT DOCUMENTS

| | | |
|---|---|---|
| 2,849,002 A | 8/1958 | Oddo |
| 3,154,077 A | 10/1964 | Cannon |
| 3,640,282 A | 2/1972 | Kamen et al. |
| 3,648,294 A | 3/1972 | Shahrestani |
| 3,850,176 A | 11/1974 | Gottschalk |
| 3,889,685 A | 6/1975 | Miller, Jr. et al. |
| 4,261,339 A | 4/1981 | Hanson et al. |
| 4,292,974 A | 10/1981 | Fogarty et al. |
| 4,327,736 A | 5/1982 | Inoue |
| 4,338,942 A | 7/1982 | Fogarty |
| 4,402,307 A | 9/1983 | Hanson et al. |
| 4,467,790 A | 8/1984 | Schiff |
| 4,531,512 A | 7/1985 | Wolvek et al. |
| 4,848,344 A * | 7/1989 | Sos et al. ................... 128/344 |
| 4,917,088 A | 4/1990 | Crittenden |

(List continued on next page.)

FOREIGN PATENT DOCUMENTS

| | | |
|---|---|---|
| EP | 0 274 411 | 7/1988 |
| EP | 0 597 465 | 9/1988 |
| EP | 0 135 990 | 9/1990 |
| EP | 0 410 072 | 1/1991 |
| EP | 0 436 501 | 4/1993 |
| EP | 0 420 488 | 7/1993 |
| EP | 0 439 202 | 9/1993 |
| EP | 0 592 885 | 9/1993 |
| EP | 0 318 919 | 1/1994 |
| EP | 0 383 794 | 6/1994 |
| EP | 0 355 937 | 11/1995 |
| EP | 0 713 712 | 5/1996 |
| EP | 0 730 879 | 9/1996 |
| EP | 0 531 117 | 1/1997 |
| EP | 0 362 826 | 5/1997 |
| EP | 0 566 684 | 6/1997 |
| EP | 0 779 062 | 6/1997 |
| EP | 0 826 395 | 3/1998 |

*Primary Examiner*—David O. Reip
(74) *Attorney, Agent, or Firm*—Ryan Kromholz & Manion, S.C.

(57) ABSTRACT

An expandable structure made from an elastomer material is preformed to a desired geometry by exposure to heat and pressure. The structure undergoes controlled expansion and further distention in cancellous bone, with controlled deformation and without failure.

11 Claims, 5 Drawing Sheets

U.S. PATENT DOCUMENTS

| | | | |
|---|---|---|---|
| 4,969,888 A | 11/1990 | Scholten et al. | |
| 4,983,167 A | 1/1991 | Sahota | |
| 5,102,390 A | 4/1992 | Crittenden et al. | |
| 5,104,376 A | 4/1992 | Crittenden | |
| 5,108,404 A | 4/1992 | Scholten et al. | |
| 5,295,994 A | 3/1994 | Bonutti | |
| 5,352,199 A | 10/1994 | Tower | |
| 5,415,635 A | 5/1995 | Bagaoisan et al. | |
| 5,587,125 A | 12/1996 | Roychowdhury | |
| 5,766,151 A | * 6/1998 | Valley et al. | 604/96 |
| 5,827,289 A | * 10/1998 | Reiley et al. | 606/86 |
| 5,938,582 A | * 8/1999 | Ciamacco, Jr. et al. | 600/3 |
| 5,972,015 A | 10/1999 | Scribner et al. | |
| 6,048,346 A | 4/2000 | Reiley | |
| 6,066,154 A | 5/2000 | Reiley et al. | |
| D439,980 S | 4/2001 | Reiley et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,379,373 B1 | 4/2002 | Sawhney et al. | |
| 6,383,212 B2 | 5/2002 | Durcan et al. | |

FOREIGN PATENT DOCUMENTS

| | | |
|---|---|---|
| EP | 0 834 293 | 4/1998 |
| WO | WO89/02763 | 4/1989 |
| WO | WO91/17788 | 11/1991 |
| WO | WO92/11892 | 7/1992 |
| WO | WO92/19440 | 11/1992 |
| WO | WO94/02197 | 2/1994 |
| WO | WO95/20362 | 8/1995 |
| WO | WO95/22367 | 8/1995 |
| WO | WO96/04951 | 2/1996 |
| WO | WO96/12516 | 5/1996 |
| WO | WO96/39970 | 12/1996 |
| WO | WO97/03716 | 2/1997 |
| WO | WO97/17098 | 5/1997 |
| WO | WO97/17099 | 5/1997 |
| WO | WO97/40877 | 11/1997 |
| WO | WO98/03218 | 1/1998 |
| WO | WO 98/56301 | 12/1998 |
| WO | WO 99/29246 | 6/1999 |
| WO | WO 00/37212 | 7/1999 |
| WO | WO 99/51149 | 10/1999 |
| WO | WO 99/62416 | 12/1999 |
| WO | WO 01/28439 | 4/2001 |
| WO | WO 01/76514 | 10/2001 |

* cited by examiner

EXPANDABLE PREFORMED STRUCTURES FOR DEPLOYMENT IN INTERIOR BODY REGIONS

RELATED APPLICATION

This application is a continuation-in-part of U.S. patent application Ser. No. 09/088,459, filed Jun. 1, 1998, now abandoned.

This application is also a continuation-in-part of U.S. patent application Ser. No. 08/788,786, filed Jan. 23, 1997, now U.S. Pat. No. 6,235,043, which is a continuation of U.S. patent application Ser. No. 08/188,224, filed Jan. 26, 1994 (now abandoned).

FIELD OF THE INVENTION

The invention relates to expandable structures, which, in use, are deployed in interior body regions of humans and other animals.

BACKGROUND OF THE INVENTION

The deployment of expandable structures, generically called "balloons," into cancellous bone is known. For example, U.S. Pat. Nos. 4,969,888 and 5,108,404 disclose apparatus and methods using expandable structures in cancellous bone for the fixation of fractures or other osteoporotic and non-osteoporotic conditions of human and animal bones.

SUMMARY OF THE INVENTION

When deployed in cancellous bone, expandable structures should undergo expansion and distention without failure. Furthermore, such structures, when distended, should generally match the geometry of the interior bone space in which the structure is deployed. In addition, such structures should permit compaction of areas of lowest bone density. Exposure to cancellous bone also typically requires materials having resistance to surface abrasion and/or tensile stresses.

It is has been determined that expandable structures incorporating elastomer materials, e.g., polyurethane, which have been preformed to a desired shape, e.g., by exposure to heat and pressure, can undergo controlled expansion and further distention in cancellous bone, without failure, while exhibiting resistance to surface abrasion and puncture when contacting cancellous bone.

Features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The preferred embodiment describes improved systems and methods that embody features of the invention in the context of treating bones. This is because the new systems and methods are advantageous when used for this purpose. However, aspects of the invention can be advantageously applied for diagnostic or therapeutic purposes in other areas of the body.

The new systems and methods will be more specifically described in the context of the treatment of human vertebra. Of course, other human or animal bone types can be treated in the same or equivalent fashion.

I. Anatomy of a Vertebral Body

Figure 1:
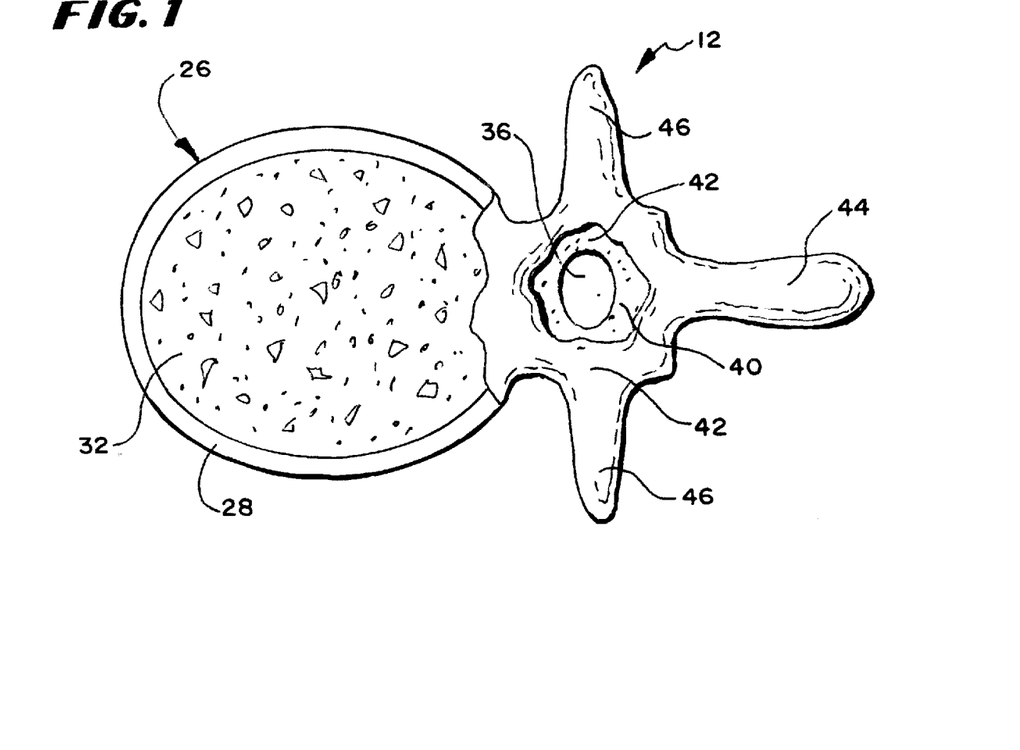
FIG. 1 is a coronal view of a vertebral body.
Figure 2:
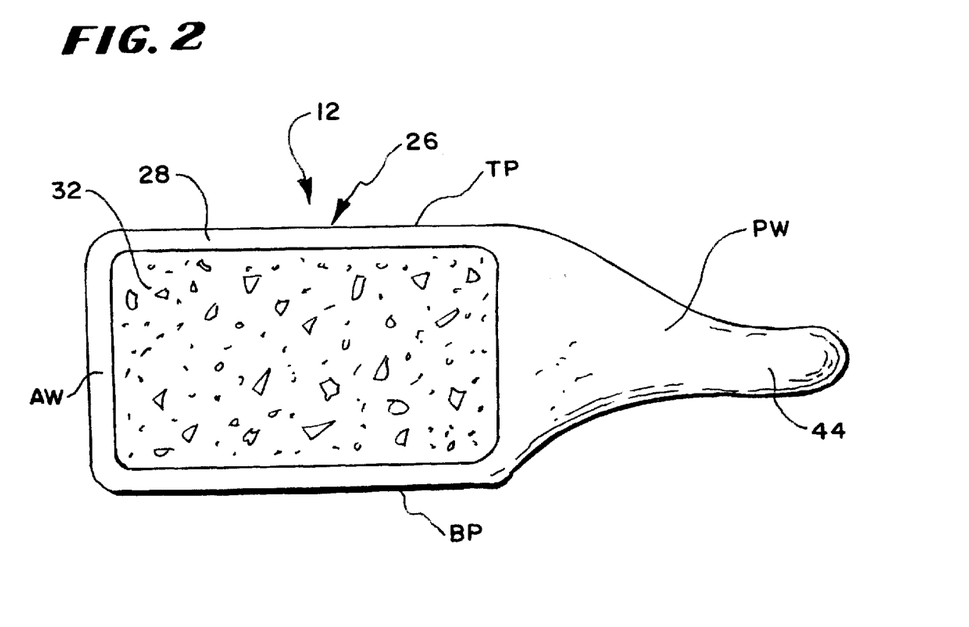
FIG. 2 is a lateral view of the vertebral body shown in FIG. 1.

FIG. 1 shows a coronal (top) view of a human lumbar vertebra 12. FIG. 2 shows a lateral (side) view of the vertebra 12. The vertebra 12 includes a vertebral body 26, which extends on the anterior (i.e., front or chest) side of the vertebra 12. The vertebral body 26 is shaped generally like a marshmallow.

As FIGS. 1 and 2 show, the vertebral body 26 includes an exterior formed from compact cortical bone 28. The cortical bone 28 encloses an interior volume of reticulated cancellous, or spongy, bone 32 (also called medullary bone or trabecular bone).

The spinal canal 36 (see FIG. 1), is located on the posterior (i.e., back) side of each vertebra 12. The spinal cord (not shown) passes through the spinal canal 36. The vertebral arch 40 surrounds the spinal canal 36. Left and right pedicles 42 of the vertebral arch 40 adjoin the vertebral body 26. The spinous process 44 extends from the posterior of the vertebral arch 40, as do the left and right transverse processes 46.

It may be indicated, due to disease or trauma, to compress cancellous bone within the vertebral body. The compression, for example, can be used to form an interior cavity, which receives a filling material, e.g., a flowable material that sets to a hardened condition, like bone cement, allograft tissue, autograft tissue, hydroxyapatite, or synthetic bone substitute, as well as a medication, or combinations thereof, to provide improved interior support for cortical bone or other therapeutic functions, or both. The compaction of cancellous bone also exerts interior force upon cortical bone, making it possible to elevate or push broken and compressed bone back to or near its original prefracture, or other desired, condition.

II. Tool for Treating Vertebral Bodies

Figure 3:
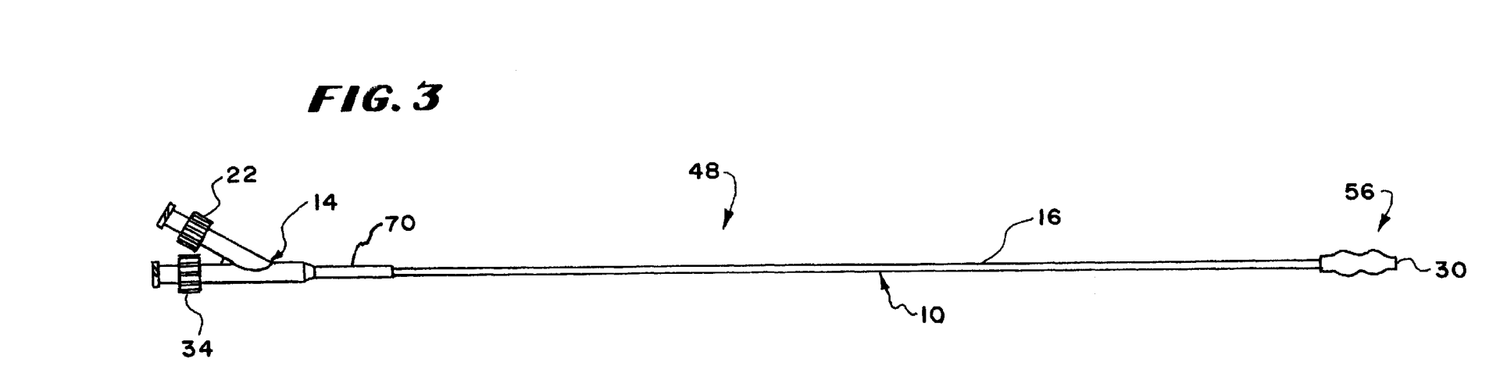
FIG. 3 is a plan view of a tool which carries at its distal end an expandable structure that embodies features of the invention.
Figures 4, 5:
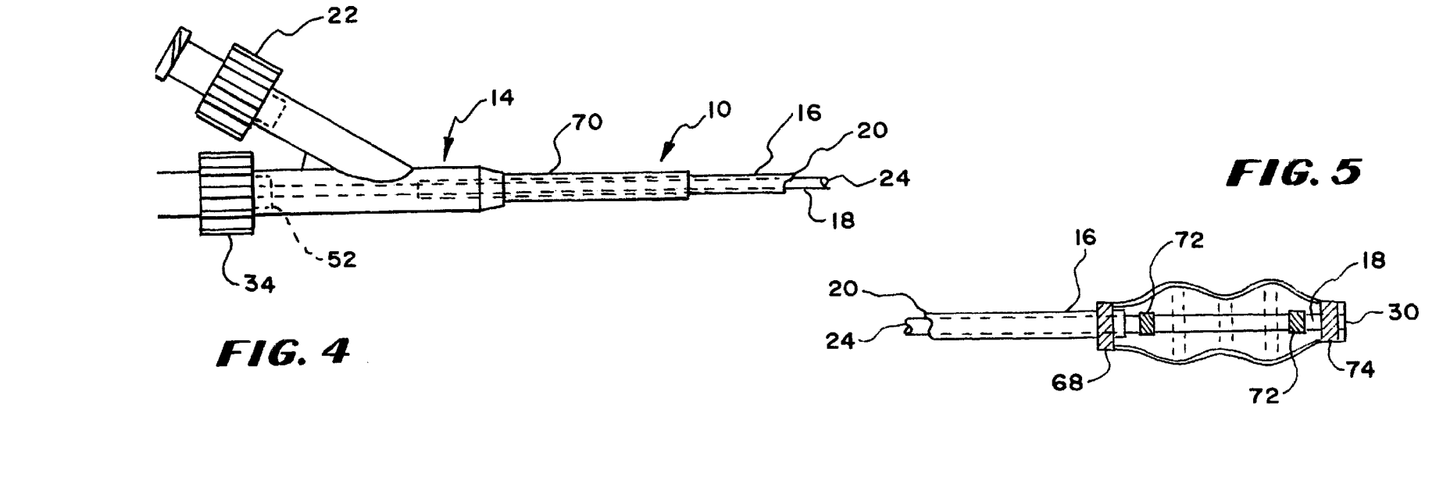
FIG. 4 is an enlarged view of the proximal end of the tool shown in FIG. 3, showing the handle and connected luer fittings.
FIG. 5 is an enlarged view of the distal end of the tool shown in FIG. 3, showing the expandable structure.

FIGS. 3 to 5 show a tool 48 for accessing bone for the purpose of compacting cancellous bone. The tool 48 includes a catheter tube assembly 10. The distal end of the catheter tube assembly 10 carries an expandable structure 56. In use, the structure is deployed and expanded inside bone, e.g., in the vertebral body 26 shown in FIGS. 1 and 2, to compact cancellous bone 32, as will be described later.

As best shown in FIGS. 4 and 5, the catheter tube assembly 10 includes an outer catheter body 16 and an inner catheter body 18, which extends through the outer catheter body 16. The proximal ends of the outer and inner catheter bodies 16 and 18 are coupled to a y-shaped adaptor/handle 14 (as FIG. 4 shows).

As FIG. 5 shows, the expandable structure 56 is coupled at its proximal end to the distal end of the outer catheter body 16. Likewise, the expandable structure is coupled at its distal end to the distal end of the inner catheter body 18.

The outer catheter body 16 defines an interior lumen 20 (see FIGS. 4 and 5), through which the inner catheter body 18 extends. In use, the interior lumen 20 conveys a pressurized liquid, e.g., sterile water, radiopaque fluid (such as CONRAY™ solution, from Mallinkrodt, Inc., or an other fluid into the structure 56, to expand it.

A first female-to-male luer fitting 22 is secured to the handle 14 and serves, in use, to couple the interior lumen 20 to a source of pressured liquid.

As FIGS. 4 and 5 also show, the inner catheter body 18 defines an interior lumen 24, which passes concentrically through the interior lumen 20 of the outer catheter body 16. In use, the interior lumen 24 can serve to convey a flushing liquid, e.g., sterile saline, for discharge through an opening 30 at the distal end of the inner catheter body 18.

A second female-to-male luer fitting 34, which is joined to the inner catheter body 18, is also secured to the handle 14. If desired, the second female-to-male luer fitting 34 can serve to couple the interior lumen 24 to a source of flushing liquid. In addition, the interior lumen 24 of the inner catheter body 18 can accommodate passage of a stylet 38 (see FIG. 6). The distal end of the stylet 38 is preferably radiused, to prevent puncture of the inner catheter body 18.

Figure 6:
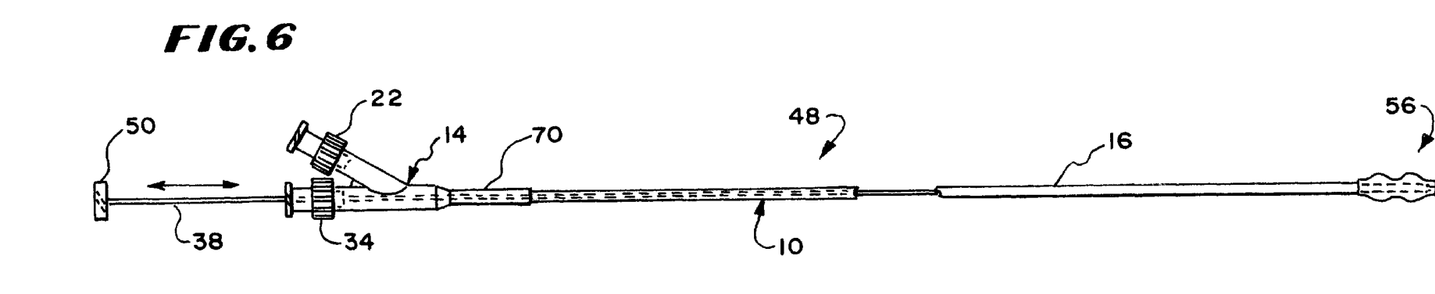
FIG. 6 is a plan view of the tool shown in FIG. 3, also showing a stylet that can be inserted into the tool to straighten the expandable structure during deployment in bone.

As FIG. 6 shows, the stylet 38 desirably carries a screw cap 50, which when attached to the second luer fitting 34, holds the stylet 38 in place within the inner catheter body 18. In the illustrated embodiment, the proximal end of the inner catheter body 18 includes a flared region 52 (see FIG. 4) where it joins the second luer fitting 34. The flared region 52 allows smooth insertion of the stylet 38, free of interference or contact with the peripheral edge of the inner catheter body 18.

When the cap 50 is screwed into the second luer fitting 34, the stylet 38 desirably extends through the entire interior lumen 24 of the inner catheter body 18. In the illustrated embodiment, the opening 30 at the distal end of the inner catheter body 18 is sized to block passage of the stylet 38 beyond the distal end of the inner catheter body 18. Thus, when inserted through the interior lumen 24 and locked to the handle 14 with the screw cap 50, the stylet 38 desirably abuts against the distal end of the structure 56. The presence of the stylet 38 desirably prevents the structure 56 from bunching or deflecting when the structure 56 is inserted into the cannula 78 and/or bone.

Figure 7:
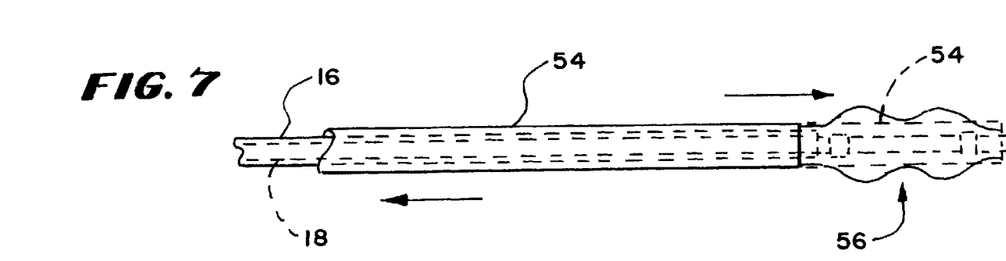
FIG. 7 is an enlarged view of the distal end of the tool shown in FIG. 3, also showing an insertion sleeve that can be used to compact the expandable structure prior to insertion into a cannula.

The tool 48 also includes an insertion sleeve 54 (see FIG. 7). The insertion sleeve 54 is carried for sliding movement along the outer catheter body 16. The insertion sleeve 54 slides forward over the structure 56 (shown in phantom lines in FIG. 7), to protect and compress the structure 56 during its insertion into the cannula 78. Once the structure 56 is deployed into the cannula 78, the insertion sleeve 54 slides aft away from the structure 56 (shown in solid lines in FIG. 7), and can, if desired, engage the handle 14.

Various materials can be selected for the component parts of the tool 48. Furthermore, the dimensions of the component parts of the tool 48 can also vary, according to its intended use. The following table lists preferred component materials and dimensions, which are well suited for a tool 48 that can be deployed for use in a vertebral body:

| Component | Material | Dimension (Inches) |
| --- | --- | --- |
| Outer catheter body 16 | 99% TEXIN ® 5270 Polyurethane 1% Titanium Dioxide (Colorant) | Outside Diameter: 0.102 Inside Diameter: 0.078 |
| Inner catheter body 18 | A Blend Comprising: 25% TEXIN ® 5286 Polyurethane 75% TEXIN ® 5270 Polyurethane | Outside Diameter: 0.063 Inside Diameter: 0.043 |
| Expandable Structure | TEXIN ® 5286 Polyurethane | As Formed: Axial Length (From Distal End of Outer Catheter Tube to Distal end of Inner Catheter Tube): 0.949 Compressed Diameter: 0.160" Non-Expanded Diameter: 0.270" |
| Tool | | Total End to End Length: 15.75 |
| Stylet | Stainless Steel | Outside Diameter: 0.038 |
| Insertion sleeve 54 | PEBAX ® Tubing | Outside Diameter: 0.195 Inside Diameter: 0.160 Length: 1.5 |

The blend of polyurethane materials for the inner catheter body 18 desirably enhances the strength of the distal bond between the inner catheter body 18 and the structure 56, due to the presence in both components of the common TEXIN® 5286 Polyurethane material. This improved bond allows the length of the distal bond to be reduced without sacrificing bond integrity. In addition, because both the inner catheter body 18 and the structure 56 are clear plastic, visual inspection of the distal bond area is simplified.

The component parts of the tool 48 can be formed and assembled in various ways. A preferred assembly will now be described.

A. The Expandable Structure

The material from which the structure 56 is made should possess various physical and mechanical properties to optimize its functional capabilities to compact cancellous bone. The three most important properties are the ability to expand its volume; the ability to deform in a desired way when expanding and assume a desired shape inside bone; and the ability to withstand abrasion, tearing, and puncture when in contact with cancellous bone.

1. Expansion Property

A first desired property for the structure material is the ability to expand or otherwise increase its volume without failure. This property enables the structure 56 to be deployed in a collapsed, low profile condition subcutaneously, e.g., through a cannula, into the targeted bone region. This property also enables the expansion of the structure 56 inside the targeted bone region to press against and compress surrounding cancellous bone, or move cortical bone to a prefracture or other desired condition, or both.

The desired expansion property for the structure material can be characterized by ultimate elongation properties, which indicate the degree of expansion that the material can accommodate prior to failure. Sufficient ultimate elongation permits the structure 56 to compact cortical bone, as well as lift contiguous cortical bone, if necessary, prior to wall failure. Desirably, the structure 56 will comprise material able to undergo an ultimate elongation of at least 50%, prior to wall failure. when expanded outside of bone. More desirably, the structure will comprise material able to undergo an ultimate elongation of at least 150%, prior to wall failure, when expanded outside of bone. Most desirably, the structure will comprise material able to undergo an ultimate elongation of at least 300%, prior to wall failure, when expanded outside of bone.

2. Shape Property

A second desired property for the material of the structure 56 is the ability to predictably deform during expansion, so that the structure 56 consistently achieves a desired shape inside bone.

The shape of the structure 56, when expanded in bone, is desirably selected by the physician, taking into account the morphology and geometry of the site to be treated. The shape of the cancellous bone to be compressed, and the local structures that could be harmed if bone were moved inappropriately, are generally understood by medical professionals using textbooks of human skeletal anatomy along with their knowledge of the site and its disease or injury, and also taking into account the teachings of U.S. patent application Ser. No. 08/788,786, filed Jan. 23, 1997, and entitled "Improved Inflatable Device for Use in Surgical Protocol Relating to Fixation of Bone," which is incorporated herein by reference. The physician is also desirably able to select the desired expanded shape inside bone based upon prior analysis of the morphology of the targeted bone using, for example, plain film x-ray, fluoroscopic x-ray, or MRI or CT scanning. The expanded shape inside bone is selected to optimize the formation of a cavity that, when filled with a selected material, provides support across the region of the bone being treated. The selected expanded shape is made by evaluation of the predicted deformation that will occur with increased volume due to the shape and physiology of the targeted bone region.

In some instances, it is desirable, when creating a cavity, to also move or displace the cortical bone to achieve the desired therapeutic result. Such movement is not per se harmful, as that term is used in this Specification, because it is indicated to achieve the desired therapeutic result. By definition, harm results when expansion of the structure 56 results in a worsening of the overall condition of the bone and surrounding anatomic structures, for example, by injury to surrounding tissue or causing a permanent adverse change in bone biomechanics.

As one general consideration, in cases where the bone disease causing fracture (or the risk of fracture) is the loss of cancellous bone mass (as in osteoporosis), the selection of the expanded shape of the structure 56 inside bone should take into account the cancellous bone volume which should be compacted to achieve the desired therapeutic result. An exemplary range is about 30% to 90% of the cancellous bone volume, but the range can vary depending upon the targeted bone region. Generally speaking, compacting less of the cancellous bone volume leaves more uncompacted, diseased cancellous bone at the treatment site.

Another general guideline for the selection of the expanded shape of the structure 56 inside bone is the amount that the targeted fractured bone region has been displaced or depressed. The controlled deformation diameter expansion of the structure 56 within the cancellous bone region inside a bone can elevate or push the fractured cortical wall back to or near its anatomic position occupied before fracture occurred. Generally speaking, inadequate compaction of cancellous bone results in less lifting of contiguous cortical bone.

For practical reasons, it is desired that the expanded shape of the structure 56 inside bone, when in contact with cancellous bone, substantially conforms to the shape of the structure 56 outside bone, when in an open air environment. This allows the physician to select in an open air environment a structure having an expanded shape desired to meet the targeted therapeutic result, with the confidence that the expanded shape inside bone will be similar in important respects.

An optimal degree of shaping can be achieved by material selection and by special manufacturing techniques, e.g., thermoforming or blow molding, as will be described in greater detail later.

3. Toughness Property

A third desired property for the structure 56 is the ability to resist surface abrasion, tearing, and puncture when in contact with cancellous bone. This property can be characterized in various ways.

One way of measuring a material's resistance to abrasion, tearing and/or puncture is by a Taber Abrasion test. A Taber Abrasion test evaluates the resistance of a material to abrasive wear. For example, in a Taber Abrasion test configured with an H-18 abrasive wheel and a 1 kg load for 1000 cycles (ASTM Test Method D 3489), Texin® 5270 material exhibits a Taber Abrasion value of approximately 75 mg loss. As another example, under the same conditions Texin® 5286 material exhibits a Taber Abrasion value of approximately 30 mg loss. Typically, a lower Taber Abrasion value indicates a greater resistance to abrasion. Desirably, the structure will comprise material having a Taber Abrasion value under these conditions of less than approximately 200 mg loss. More desirably, the structure will comprise material having a Taber Abrasion value under these conditions of less than approximately 145 mg loss. Most desirably, the structure will comprise material having a Taber Abrasion value under these conditions of less than approximately 90 mg loss.

Another way of measuring a material's resistance to abrasion, tearing and/or puncture is by Elmendorf Tear Strength. For example, under ASTM Test Method D 624, Texin® 5270 material exhibits a Tear Strength of 1,100 lb-ft/in. As another example, under the same conditions, Texin 5286 exhibits a Tear Strength of 500 lb-ft/in. Typically, a higher Tear Strength indicates a greater resistance to tearing. Desirably, the structure will comprise material having a Tear Strength under these conditions of at least approximately 150 lb-ft/in. More desirably, the structure will comprise material having a Tear Strength under these conditions of at least approximately 220 lb-ft/in. Most desirably, the structure will comprise material having a Tear Strength under these conditions of at least approximately 280 lb-ft/in.

Another way of measuring a material's resistance to abrasion, tearing and/or puncture is by Shore Hardness. For example, under ASTM Test Method D 2240, Texin® 5270 material exhibits a Shore Hardness of 70D. As another example, under the same conditions, Texin® 5286 material exhibits a Shore Hardness of 86A. Typically, a lower Shore Hardness number on a given scale indicates a greater degree of elasticity, flexibility and ductility. Desirably, the structure will comprise material having a Shore Hardness under these conditions of less than approximately 75D. More desirably, the structure will comprise material having a Shore Hardness under these conditions of less than approximately 65D. Most desirably, the structure will comprise material having a Shore Hardness under these conditions of less than approximately 100A.

It should be noted that a structure incorporating a plurality of materials, such as layered materials and/or composites, may possess significant resistance to surface abrasion, tearing and puncture. For example, a layered expandable structure incorporating an inner body formed of material having a Taber Abrasion value of greater than 200 mg loss and an outer body having a shore hardness of greater than 75D might possess significant resistance to surface abrasion, tearing and puncture. Similarly, other combinations of materials could possess the desired toughness to accomplish the desired goal of compressing cancellous bone and/or moving cortical bone prior to material failure.

4. Creating a Pre-Formed Structure

The expansion and shape properties just described can be enhanced and further optimized for compacting cancellous bone by selecting an elastomer material, which also possess the capability of being preformed, i.e., to acquire a desired shape by exposure, e.g., to heat and pressure, e.g., through the use of conventional thermoforming or blow molding techniques. Candidate materials that meet this criteria include polyurethane, silicone, thermoplastic rubber, nylon, and thermoplastic elastomer materials.

As described earlier, in the illustrated embodiment, TEXIN® 5286 polyurethane material is used. This material is commercially available from Bayer in pellet form.

The pellets can be processed and extruded in a tubular shape using, e.g., a screw type (888 4:1) extrusion machine, with a GENCA™ head, with a single finger spider and a 80–100–200 screen. The following table summarizes representative process settings for the extrusion.

| Extrusion Element | Nominal Setting |
| --- | --- |
| Die | 0.338" |
| Mandrel | 0.180" |
| Zone 1 Set/Actual | 270 degrees F |
| Zone 2 Set/Actual | 370 degrees F |
| Zone 3 Set/Actual | 380 degrees F |
| Melt Temperature | 405 degrees F |
| Clamp Set/Actual | 370 degrees F |
| Adaptor Set/Actual | 380 degrees F |
| Die 1 Set/Actual | 380 degrees F |
| Die 2 Set/Actual | 380 degrees F |
| Extruder | 1600 RPM |
| Barrel | 1600 PSI |
| Motor | 5 Amps |

| Extrusion Element | Nominal Setting |
| --- | --- |
| Mandrel Air | 2" of water |
| Entry Hole Diameter | 0.3" |
| Bath Dist. from Tooling | 1" |
| Water Flow/Temperature | 6 GPH/70 degrees F |
| Air Wipe | 20 PSI |
| Speed | 21.5 FPM |
| Min Dryer Time/Temperature | Overnight/160 degrees F |

The ultimate dimensions of the tubular extrusion can vary, according to the desired size and shape of the structure 56. In a representative embodiment, the tubular extrusion has an outside diameter of 0.164", and inner diameter of 0.092", and a wall diameter of 0.36". Reasonable processing tolerances can of course be established The tubular extrusion is cut into individual lengths for further processing. The tube length can vary, according to the desired configuration of the structure 56. In a representative embodiment, each tube is cut to a length of about 48" for further processing.

Figure 8:
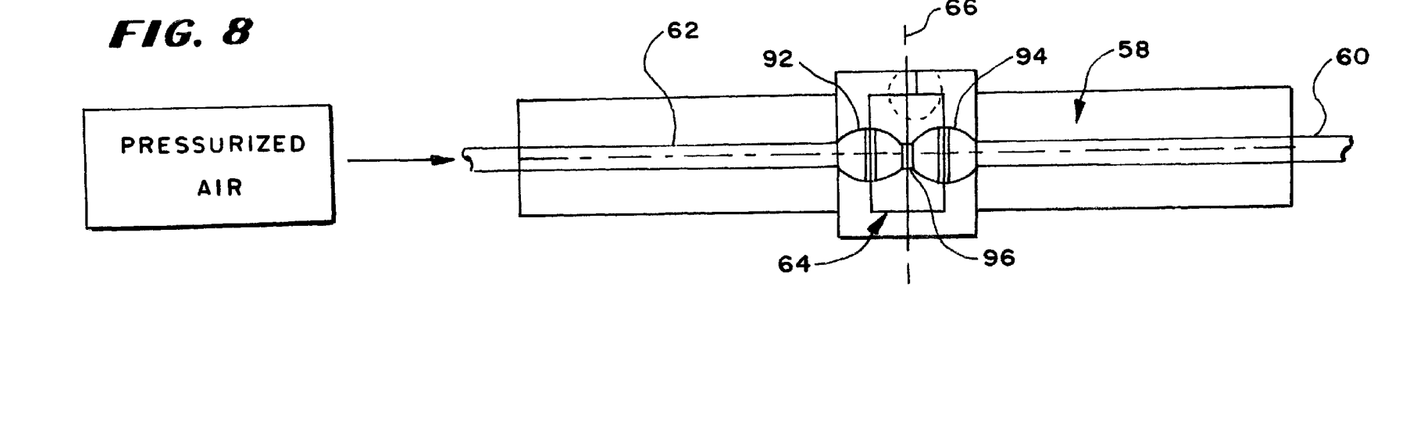
FIG. 8 is a top view of a mold forming the expandable structure shown in FIG. 5.

The structure 56 is formed by exposing a cut tube length 60 to heat and then enclosing the heated tube 60 within a mold 58 while positive interior pressure is applied to the tube length 60. The mold 10 can be part of a conventional balloon forming machine, such as the Model No. 9608C made by Interface Associates.

As FIG. 8 shows, the mold 58 includes a tube holding channel 62, through which the tube length 60 extends for processing. The holding channel 62 includes a formed intermediate cavity 64, which possesses a desired geometry. The cavity 64 defines the geometry intended for the structure 56.

In the illustrated embodiment, the cavity 64 possesses two enlarged cavity spaces 92 and 94 with an intermediate channel 96. The dimensions of the spaces 92, 94 and channel 96 can, of course, vary according to the desired dimensions of the structure 56.

In a representative embodiment, each enlarged cavity space 92 and 94 extends 0.395" on each side of the center line 66. The maximum diameter of each cavity space 92 and 94 is 0.314", and the maximum diameter for the spacing channel 96 is 0.174". Desirably, all surfaces within the mold 58 are radiused to provide a smooth transition.

Prior to heating, one end of the tube length 60 is attached to a source of pressurized air, e.g., nitrogen. The other end of the tube length 60 is gripped and closed. The tube is desirably subjected to a tensioning force (e.g., 16 oz).

The tube length 60 is then subjected to a heating cycle. During the heating cycle, the tube length 60 is heated to a predetermined heated temperature for a set dwell time. The heated temperature and dwell time are selected to soften the tube length 60 for subsequent stretching and pressure shaping.

The range of heated temperatures in which softening occurs will depend upon the particular composition of the polymeric material used. For example, for the polyurethane tube of the dimensions described above, a heated temperature of 290 degrees F. and a dwell time of 220 seconds can be used. An operating range of softening temperatures for a given plastic material can be empirically determined. Suitable processing tolerances can also be empirically established.

When the heating cycle ends, the heat-softened tube length 60 is stretched by pulling it a set amount. The stretching desirably reduces the thickness of the tube walls.

In a representative embodiment, the tube is stretched approximately 0.198" to each side. The amount of stretching is selected to facilitate shaping without significantly reducing the resistance of the material, once shaped, to puncture.

The mold 58 then closes over the heated and stretched tube length 60. Pressurized air (typically, nitrogen) is introduced through the interior of the tube length 60 for a set amount of dwell time at a set flow rate. The magnitude of pressure, dwell time, and flow rate will vary, depending upon the wall thickness and other physical characteristics of the material used. For the polyurethane tube of the dimensions described, a pressure of 100 PSI at a flow rate of 0.4 l/min for a dwell time of 45 seconds can be used.

The introduction of pressurized air into tube length 60 causes the tube region located within the cavity 64 to expand or billow outward, forming the structure 56. The cavity 64 limits the extent to which the structure 56 expands. The structure 56, upon expansion in the cavity 64, will desirably conform to the geometry of the cavity 64. During the pressurization phase, the flow of pressurized air can be used to help cool the tube length 60.

After the pressurization phase, the tube length 60 is removed from the mold. The source of pressurized air is detached. Excess material on both sides of the formed structure region is discarded. Preferably, at least one inch of tube material is left on each side of the formed structure region to aid handling and identification during further processing.

B. Assembly of the Tool

1. Assembling the Outer Catheter Body

In a representative embodiment, the outer catheter body 16 comprises an extruded tube, made from 99% TEXIN® 5270 Material and 1% Titanium Dioxide. The TEXIN® material can be purchased in pellet form from Bayer. The outer catheter body can be extruded in a tubular shape using, e.g., a screw type (888 4:1) extrusion machine, with a GENCA™ head, with a single finger spider and a C5WB23 screen. The following table summarizes representative process settings for the extrusion.

| Extrusion Element | Nominal Setting |
| --- | --- |
| Die | 0.203" |
| Mandrel | 0.150" |
| Zone 1 Set/Actual | 300 degrees F |
| Zone 2 Set/Actual | 340 degrees F |
| Zone 3 Set/Actual | 400 degrees F |
| Clamp Set/Actual | 24.6 degrees F |
| Adaptor Set/Actual | 400 degrees F |
| Die 1 Set/Actual | 400 degrees F |
| Die 2 Set/Actual | 400 degrees F |
| Extruder | 400 RPM |
| Motor | In. 2300 Auto/Dis. 2929 |
| Mandrel Air | 5.2 PSI |
| Entry Hole Diameter-Distribution | 300-½" |
| Water Flow/Temperature | 20 ccm |
| Air Wipe | 20 PSI |
| Speed | 39 FPM |
| Min Dryer Time/Temperature | Overnight/160 degrees F |

The extrusion is initially cut to lengths of 16" for assembly.

Each tubing length comprising an outer catheter body 16 preferably undergoes annealing, e.g., by oven curing at 60 to 70 degrees C. for 2 to 6 hours. Annealing reduces the incidence of shrinkage of the outer catheter body 16 during sterilization and/or storage prior to use.

The proximal end of the structure 56 is heat bonded to the distal end of the outer catheter body 16 in the presence of an overlying ring of silicone tubing 68 (see FIG. 5), which compresses the outer catheter body 16 and the proximal end of the structure 56 together during the heat bonding process. In one representative assembly technique, a support mandrel (e.g., having an outside diameter of 0.075") is inserted within the outer catheter body 16, and the proximal end of the structure 56 is slid over the distal end of the outer catheter body 16. A length of the silicone tubing 68 (having, e.g., an initial inside diameter of 0.104") is subsequently slid over the proximal end of the structure 56 and the catheter body 16. Heat from the heat box is applied to the silicone tubing, and the structure and outer catheter body 16 fuse together. The silicone tubing is then discarded.

For the materials and dimensions described, representative settings for the heat box are a temperature of 545 degrees F., an air flow of 40 SCFH, and an air pressure of 20 to 30 PSI. At this setting, the silicone tubing 68 and junction of the structure 56 and the outer catheter body 16 are exposed to heat for 60 seconds, and are rotated 180 degrees after the first 30 seconds. The resulting heat bond is allowed to cool.

The outer catheter body 16 can then be cut to a desired final length, e.g., which in a representative embodiment is 350 mm measured from the center of the structure 56. In the illustrated embodiment (see FIG. 4), heat shrink tubing 70, which bears appropriate identification information for the tool 48, is bonded about the outer catheter body 16, about 0.5" from the proximal end of the outer catheter body 16.

A suitable UW adhesive (e.g., Dymax 204 CTH, available commercially from Dymax Corp) is applied to the proximal end of the outer catheter body 16, and the outer catheter body 16 is inserted into the handle 14. The adhesive joint is cured under UV light for an appropriate time period, e.g., 15 seconds. This secures the outer catheter body 16 and attached structure 56 to the handle 14.

2. Assembling The Inner Catheter Body

In a representative embodiment, the inner catheter body 18 comprises an extruded tube, made from 25% TEXIN® 5286 Material and 75% TEXIN® 5270 Material. The TEXIN® materials can be purchased in pellet form from Bayer.

The inner catheter body 18 can be extruded in a tubular shape using, e.g., a screw type (888 4:1) extrusion machine, with a GENCA™ head, with a 80–100–200 screen. The following table summarizes representative process settings for the extrusion.

| Extrusion Element | Nominal Setting |
| --- | --- |
| Die | 0.195" |
| Mandrel | 0.135" |
| Zone 1 Set/Actual | 360 degrees F |
| Zone 2 Set/Actual | 380 degrees F |
| Zone 3 Set/Actual | 490 degrees F |
| Clamp Set/Actual | 400 degrees F |
| Adaptor Set/Actual | 400 degrees F |
| Die 1 Set/Actual | 400 degrees F |
| Die 2 Set/Actual | 400 degrees F |
| Extruder | 30.7 RPM |
| Motor | In. 3300 Auto/Dis. 1772 |
| Mandrel Air | 1 PSI |
| Entry Hole Diameter - Distribution | 300-1" |
| Water Flow/Temperature | 20 ccm |
| Air Wipe | 20 PSI |
| Speed | 87 FPM |
| Min Dryer Time/Temperature | Overnight/160 degrees F |

The extrusion is initially cut to lengths of 16" for assembly. Like the outer catheter body 16, the inner catheter body 18 is preferably subject to heat annealing.

After annealing, the flared region 52 is formed using a 0.099" stylet heated by a heat gun. One possible setting of the heat gun is 200 degrees C. After cooling, UV adhesive is applied to secure the flared region 52 to the second luer fitting 34, which, at this stage of assembly, is not yet connected to the handle 14. The adhesive is cured under UV light for an appropriate time period.

In the illustrated embodiment (see FIG. 5), fluoroscopic marker bands 72 are secured on the inner catheter body 18. The marker bands 72 facilitate fluoroscopic visualization of the proximal and distal ends of the structure 56 on the distal end of the tool 48. In the illustrated embodiment, the marker bands 72 are made from platinum/iridium material (commercially available from Johnson Matthey).

In a representative embodiment, the marker bands 72 are located on the inner catheter body 18 about 1 mm beyond the distal end of the outer catheter body 16 and also distally about 10.6 mm from the center of the structure 56. Prior to attaching the marker bands 72, the inner catheter body 18 (stiffened by an appropriate interior support mandrel) is inserted into the outer catheter body 16, so that the desired relative positions of the marker bands 72 can be determined using a reference tool, such as a ruler. The inner catheter body 18 is then removed from outer catheter body 16, and the marker bands 72 are affixed at the indicated positions. The distal tip of inner catheter body 18 can be cut at a 45 degree angle to facilitate slipping the marker bands 72 about the body 18. The marker bands 72 are secured to the inner catheter body 18 using, e.g., a suitable adhesive primer (e.g., Loctite 7701 Primer, which is commercially available from Loctite), followed by use of a suitable adhesive (e.g. Cyanoacrylate 4061, which is commercially available from Loctite). After the adhesive cures, the inner catheter body 18 is inserted into the outer catheter body 16 and the second luer fitting 34 is secured to the handle 14 using an UV adhesive (e.g., 204-CTH Adhesive, commercially available from Dymax). The adhesive is cured by exposure to UV light for an appropriate time period. This secures the inner catheter body 18 to the handle 14.

The distal end of the inner catheter body 18 can now be secured to the distal end of the structure 56. During this operation, the dimension of the opening 30 of the inner catheter body 18 is also reduced, to block passage of the stylet 38, as previously described.

A first support mandrel (e.g., having an outer diameter of 0.041") is placed within the inner catheter body 18. A temporary ring of silicone tubing (e.g., having an inner diameter of 0.132") is slid over the junction of the distal end of the structure 56 and the distal end of the inner catheter body 18. Using a heat box, heat is applied to the silicone tubing, which causes the distal end of the stricture 56 to shrink slightly about the inner catheter body 18. This allows a smaller diameter silicone tubing to be used to form the final bond, as will be described later. Using the materials described, the heat box is set at a temperature of 525 degrees F., an air flow of 30 SCFH, and an air pressure of 20 to 30 psi. Exposure to heat desirably occurs for 16 seconds, with the assembly rotated 180 degrees after the first eight seconds.

The first support mandrel is then removed, and a reduced diameter stylet (e.g., having an outside diameter of 0.008") is inserted into the inner catheter body 18. A smaller diameter silicone tubing 74 (made, e.g., from silicone tubing having a initial inner diameter of 0.078") (see FIG. 5) is slid over the junction for final bonding of the structure 56 to the inner catheter body 18. Heat from the above-described heat box is then applied for 30 seconds to each side of the assembly. The structure-tubing interface is allowed to cool. The distal end of the structure 56 is trimmed, e.g., to a 3 mm length.

As a result of these processing steps, the inside diameter of the opening 30 is desirably reduced to a diameter that approximates the outside diameter of the reduced diameter stylet (e.g., 0.008"). This diameter is significantly smaller than the outside diameter of the stylet 38, which in the representative embodiment is 0.038". The reduced diameter of the opening 30 blocks passage of the stylet 38. Still, the reduced diameter of the opening 30 allows flushing liquid to be discharged.

The stylet 38 can now be inserted into the inner catheter body 18, with the distal end flush against the distal bond. The proximal end of the stylet 38 is secured by UV-cured adhesive (e.g., 198-M Adhesive, commercially available from Dymax) to the screw cap 50. The cap 50 can now be screwed upon the second luer fitting 34 of the handle 14.

A cut length of tubing made of Pebax™ material (e.g., 0.160 inch interior diameter) is flared at each end, using, e.g., a heat gun with a flare nozzle. This forms the insertion sleeve 54. The insertion sleeve 54 is slid over the structure 56 and onto the outer catheter body 16.

This completes the assembly of the tool 48. The tool 48 can then be packaged for sterilization in a suitable kit. If desired, the stylet 38 can be packaged next to the tool 48 to facilitate ETO sterilization, and be inserted into the inner catheter body 18 in the manner described at the time of use.

III. Use of the Tool

A. Deployment in a Vertebral Body

The structure 56 is well suited for insertion into bone in accordance with the teachings of U.S. Pat. Nos. 4,969,888 and 5,108,404, which are incorporated herein by reference.

Figure 9:
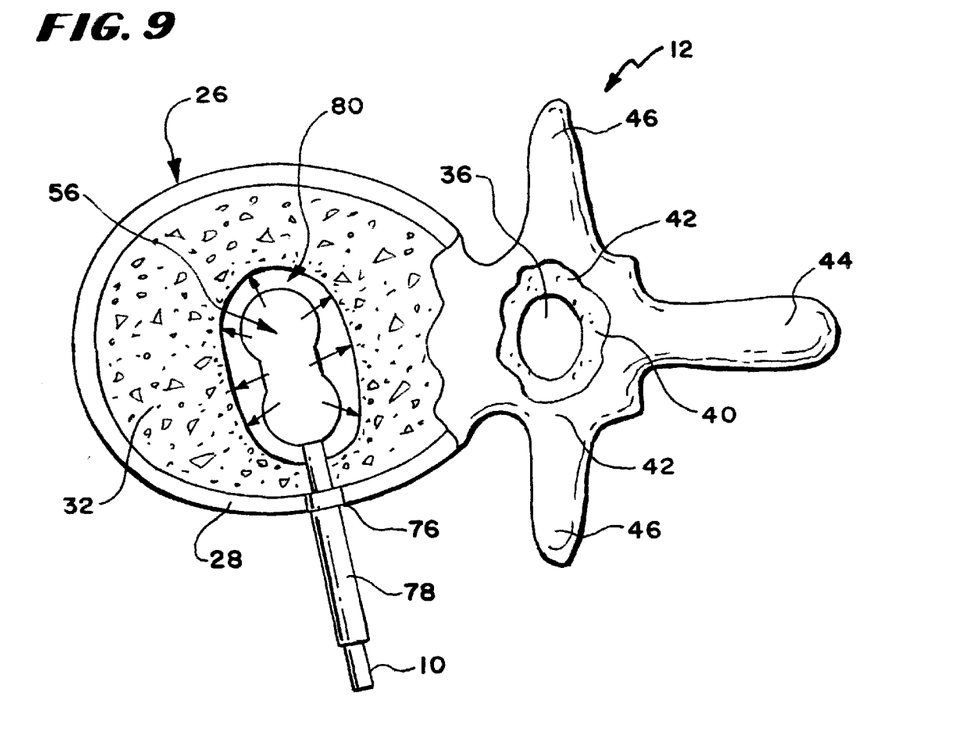
FIG. 9 is a coronal view of the vertebral body shown in FIG. 1, with the tool shown in FIG. 3 deployed to compress cancellous bone as a result of inflating the expandable structure.

For example, as FIG. 9 shows, access can be accomplished, for example, by drilling an access portal 76 through a side of the vertebral body 26. This is called a lateral approach. Alternatively, the access portal can pass through either pedicle 42, which is called a transpedicular approach. A hand held tool can be used to facilitate formation of the access portal 76, such as disclosed in copending U.S. patent application, Ser. No. 09/421,635, filed Oct. 19, 1999, and entitled "Hand Held Instruments that Access Interior Body Regions." Another hand held tool that can be used to form the access portal 76 and gain access is disclosed in copending U.S. Pat. application Ser. No. 09/014,229 filed Jan. 27, 1998 and entitled "A Slip-Fit Handle for Hand-Held Instruments that Access Interior Body Regions."

A guide sheath or cannula 78 is placed into communication with the access portal 76, which can comprise a component part of the hand held tool just described. The catheter tube assembly 10 is advanced through the cannula 78 to deploy the structure 56 into contact with cancellous bone 32. Access in this fashion can be accomplished using a closed, minimally invasive procedure or with an open procedure.

The structure 56 is passed into the bone in a normally collapsed and not inflated condition. The presence of the stylet 38 in the inner catheter body 18 serves to keep the structure 56 in the desired distally straightened condition during its passage through the cannula 78. The insertion sleeve 54 is desirably advanced over the structure 56 prior to insertion into the cannula 78, to protect and compress the structure 56. Once deployed in cancellous bone 32, the stylet 38 can be withdrawn.

As FIG. 9 shows, expansion of the structure 56 (indicated by arrows in FIG. 9) compresses cancellous bone 32 in the vertebral body 26. The compression forms an interior cavity 80 in the cancellous bone 32.

Figure 10:
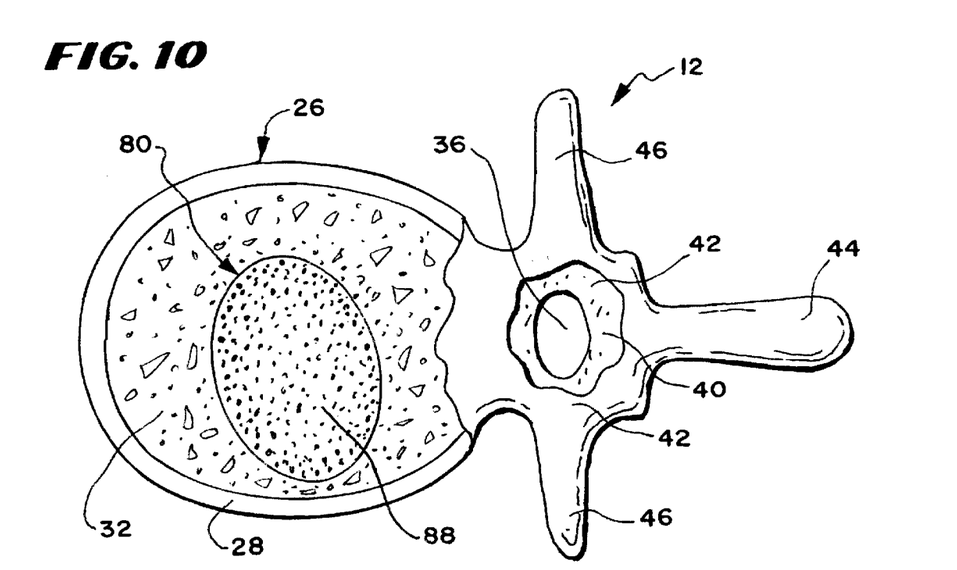
FIG. 10 is a coronal view of the vertebral body shown in FIG. 9, upon removal of the tool, showing the cavity formed by the compression of cancellous bone by the expandable structure.

As FIG. 10 shows, subsequent collapse and removal of the structure 56 leaves the cavity 80 in a condition to receive a filling material 88, e.g., bone cement, allograft tissue, autograft tissue, hydroxyapatite, or synthetic bone substitute. The material 88 provides improved interior structural support for cortical bone 32.

The compaction of cancellous bone 32, as shown in FIG. 9, can also exert an interior force upon the surrounding cortical bone 28. The interior force can elevate or push broken and compressed bone back to or near its original prefracture, or other desired, condition. In the case of a vertebral body 26, deterioration of cancellous bone 32 can cause the top and bottom plates (designated TP and BP in FIG. 2), as well as the side walls (designated AW and PW in FIG. 2), to compress, crack, or move closer together, reducing the normal physiological distance between some or all of the plates. In this circumstance, the interior force exerted by the structure 56 as it compacts cancellous bone 32 moves some or all of the plates and/or walls farther apart, to thereby restore some or all of the spacing between them, which is at or close to the normal physiological distance.

There are times when a lesser amount of cancellous bone compaction is indicated. For example, when the bone disease being treated is localized, such as in avascular necrosis, or where local loss of blood supply is killing bone in a limited area, an expandable structure 56 can compact a smaller volume of total bone. This is because the diseased area requiring treatment is smaller.

Another exception lies in the use of an expandable structure 56 to improve insertion of solid materials in defined shapes, like hydroxyapatite and components in total joint replacement. In these cases, the structure shape and size is defined by the shape and size of the material being inserted.

Yet another exception lies in the use of expandable structures in bones to create cavities to aid in the delivery of therapeutic substances, as disclosed in copending U.S. patent application Ser. No. 08/485,394, previously mentioned. In this case, the cancellous bone may or may not be diseased or adversely affected. Healthy cancellous bone can be sacrificed by significant compaction to improve the delivery of a drug or growth factor which has an important therapeutic purpose. In this application, the size of the expandable structure 56 is chosen by the desired amount of therapeutic substance sought to be delivered.

It should be understood that the filling material 88 itself could be used to expand the structure 56 within the vertebral body 26, thereby causing compaction of the cancellous bone 32 and/or movement of the cortical bone 28 as previously described. If desired, the filling material 88 within the structure 56 could be allowed to harden, and the structure 56 and hardened filling material 88 could remain within the vertebral body 26. This would significantly reduce the possibility of non-hardened filling material 88 leaking outside of the vertebral body 26. Alternatively, the pressurized fluid could be withdrawn from the structure 56 after formation of some or all of the cavity 80, and filler material 88 could be injected into the structure to fill the cavity 80 and/or complete expansion of the structure 56. As another alternative, filler material 88 could be used to expand the structure 56, and the structure 56 could subsequently be removed from the vertebral body 26 before the filling material 88 within the vertebral body 26 sets to a hardened condition.

B. Expansion Characteristics of the Structure

In the illustrated embodiment, the structure 56 is created by extruding or molding a tube 60 of a selected polyurethane material. The tube 60 is heated, stretched, and subjected to internal pressure. After stretching and pressure forming, the tube 60 has a normal wall thickness (T5) and a normal outside diameter (D5) (as shown in FIG. 11).

The segmented shaped regions 82 and 84 of the structure 56 are created by exposing the tube 86 to heat and positive interior pressure inside the cavity 64. Once formed, the structure 56 possesses, in an open air environment, a normal expanded shape, having diameter D7 (shown in phantom lines in FIG. 11). The normal shape and diameter D7 for the regions 82 and 84 generally correspond with the shape and dimension of the cavity spaces 92 and 94, respectively. When an interior vacuum is drawn, removing air from the structure 56, the structure 56 desirably assumes a substantially collapsed, and not inflated geometry, shown in phantom lines D6 in FIG. 11.

The regions 82 and 84 are separated by a tubular waist 86, which segments the structure 56 into two expandable regions 82 and 84. When substantially collapsed under vacuum or not inflated, the structure 56 desirably exhibits a low profile, ideal for insertion into the cannula and targeted cancellous bone region.

Figure 11:
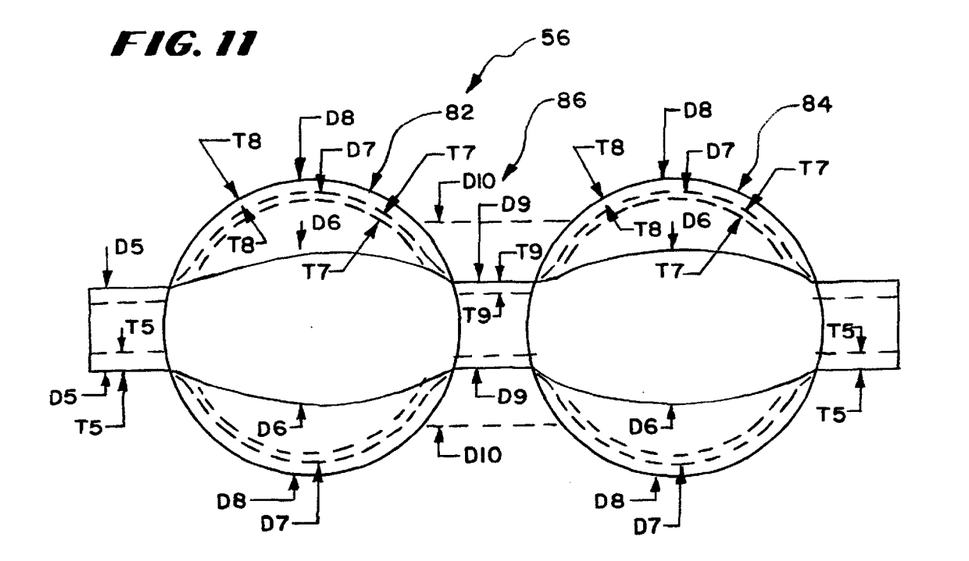
FIG. 11 is an enlarged view of the expandable structure shown in FIG. 5, diagrammatically showing the expansion characteristics of the structure.

The introduction of fluid volume back into the structure 56 will cause each region 82 and 84 to return from the collapsed diameter D6 back to the normal, enlarged, but not distended geometry, having the shape and diameter shown in phantom lines D7 in FIG. 11.

In the illustrated embodiment, the first and second shaped regions 82 and 84 have generally the same radius of expansion and thus the same non-distended shape and diameter D7. Alternatively, each region 82 and 84 can have a different radius of expansion, and thus a different non-distended shape and diameter.

Moreover, the regions 82 and 84 can be shaped by heat and interior pressure within different cavities to assume different geometries, e.g., cylindrical or elliptical geometry, or a non-spherical, non-cylindrical, or non-elliptical geometry, with either uniform or complex curvature, and in either symmetric or asymmetric forms. Of course, more than two segmented regions 82 and 84 can be formed.

Each shaped region 82 and 84 possesses a wall thickness (designed T7 in FIG. 11) when in the normally enlarged but not distended geometry D7. Due to expansion of the wall during structure formation, the wall thickness is typically not uniform along the longitudinal axis of the structure 56, i.e., T7 is typically less than the normal wall thicknesses T5 and/or T9 of the tube 60. The wall thickness T7 for the regions 82 and 84 can be the same or different.

When in the enlarged, but not distended geometry, the waist region 86 has an outside diameter (designated D9 in FIG. 11), which is desirably equal to or greater than the diameter D5 of the tube 60. The size of the channel 96 in the fixture 90 desirably determines the magnitude of the diameter D9. Due to expansion of the material during structure formation, the waist region 86 has a wall thickness (designated T9 in FIG. 11) which is less than or equal to the wall thickness T5 of the tube 60. Desirably, the wall thickness T9 of the waist region 86 is greater than the wall thickness T7 of either fully shaped region 82 or 84.

The formed complex structure 56 thus desirably possesses regions of non-uniform minimum wall thickness along its longitudinal length; that is, $T5 \geq T9 > T7$. The formed complex structure 56 also provides multiple expandable regions 82 and 84 of the same or different enlarged outside diameters (D7), segmented by a waist region 86.

By injecting additional fluid into the expandable structure 56, the shaped regions 82 and 84 of the structure 56 will desirably continue to enlarge beyond diameter D7 to a distended shape and geometry, designated D8 in FIG. 11. Typically, the wall thickness T7 further decreases and approaches T8. As the regions 82 and 84 expand, the waist region 86 will likewise expand towards diameter D10, as FIG. 11 shows. However, because the wall thickness T9 of the waist region 86 is typically greater than the wall thickness T7 of the regions 82 and 84, the waist region 86 will typically expand more slowly than the regions 82 and 84, thereby expanding the structure 56 in a more cylindrical manner, providing more uniform, elongated surface contact with cancellous bone than would a spherical expandable structure 56 of similar volume.

Enlargement of the structure 56 beyond diameter D7 desirably stretches the material in the regions 82, 84, and 86 beyond their pre-formed geometries. Desirably, these regions 82 and 84 will essentially maintain the preformed shape dictated by the cavities 92 and 94. Continued volume flow of pressurized fluid into the structure 56 continues to increase the interior volume of the structure 56 (see FIG. 12). As their volume increase, the shaped regions 82 and 84 of the structure 56 continue to enlarge beyond the normal diameter D7 toward a distended shape and geometry D8.

Of course, it should be understood that the waist region 86 could be formed of a material having different expansion characteristics than the material of the shaped regions 82 and 84, wherein a more expansion-resistant material could constrain the expansion of the waist region in a manner similar to the thickness differentials described above.

The degree of stretching and increases in volume can be tailored to achieve a desired, fully distended diameter D8. The final, fully distended diameter D8 can be selected by the treating physician, using real-time monitoring techniques, such as fluoroscopy or real-time MRI, to match the dimensions of the targeted cancellous bone region. The controlled stretching of the segmented regions 82 and 84 desirably provides compression of cancellous bone with a maximum diameter that is less than a single non-segmented region (i.e., one without the waist region 86). Stated another way, segmented regions 82 and 84, when expanded to a given inflation volume, desirably have an outer diameter less than a sphere expanded to an equal inflation volume.

While expanding in the region between D7 and D8, the structure 56, when inside bone, desirably assumes an increasingly larger surface and volume, thereby compacting surrounding cancellous bone. Inflation in cancellous bone may occur at the same pressures as outside bone. However, an increase in the inflation pressures inside bone may be required, due to the density of the cancellous bone and resistance of the cancellous bone to compaction.

Figure 12:
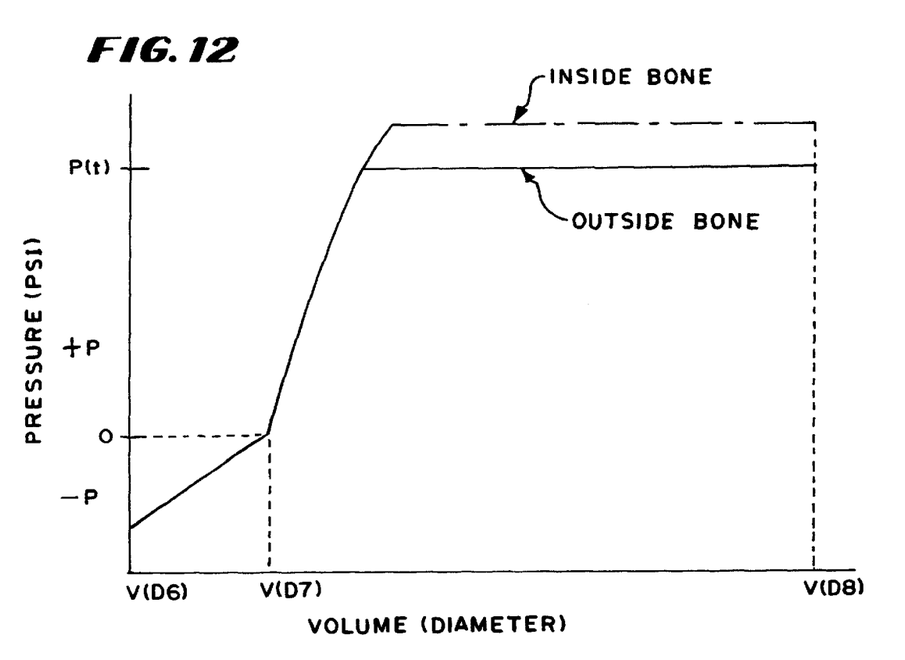
FIG. 12 is a graph which plots the effects of increasing pressure applied to the interior of the structure to the expanded volume of the structure.

For example, the configuration of the Pressure vs. Volume curve for a given material and structure 56 remains essentially the same as shown in FIG. 12, except that the generally horizontal portion of the curve between D7 and D8 is shifted upward on the Y-axis, as shown in phantom lines in FIG. 12. As a general statement, the threshold pressure inside bone is determined by the material property of the structure 56 and any added resistance due to the presence of cancellous bone.

The distance between D7 and D8, along the x-axis of FIG. 12, defines the degree to which the wall can elongate at a substantially constant pressure condition and with increasing material stress to compact cancellous bone, without failure. As volume increases at the substantially constant threshold pressure P(t), wall failure becomes more likely as the diameter of the structure enlarges significantly further beyond the distended diameter D8. There comes a point when the structure 56 can no longer increase its volume as the material elasticity approaches ultimate elongation, or as material stress approaches ultimate tensile strength. When either of these ultimate values are reached, wall failure is likely. Accordingly, the distance between D7 and D8 in FIG. 12 during expansion inside bone is a simultaneous expression of the three physical and mechanical properties— expansion, shape, and toughness—as previously described.

The features of the invention are set forth in the following claims.

We claim:

1. A device for compacting cancellous bone comprising a wall made from a flexible material, the wall peripherally defining an interior space and including an expandable region preformed with a normally expanded shape outside bone, the expandable region having proximal and distal ends, the expandable region further having a first expanded section having an interior cross-sectional area adjacent the proximal end, a second expanded section having an interior cross-sectional area adjacent the distal end, and a third section having an interior cross-sectional area located between the first and second expanded sections, the interior cross-sectional area of the third section being less than the interior cross-sectional area of either the first or second expanded sections, and the first expanded section, the second expanded section, and the third expanded section further having, respectively, a first average wall thickness, a second average wall thickness, and a third average wall thickness, and the third average wall thickness being greater than either the first average wall thickness or the second average wall thickness, the expandable region, when expanded beyond its normally expanded shape to reach a given inflation volume, presenting a maximum diameter less than a sphere expanded to an equal inflation volume.

2. A device according to claim 1 wherein the expandable region includes a further expanded shape, outside bone, having a diameter greater than the normally expanded shape.

3. A device according to claim 2 wherein the expandable region has a further expanded shape inside bone that substantially corresponds to the further expanded shape outside bone.

4. A device according to claim 1 wherein the expandable region is essentially cylindrical.

5. A device according to claim 1 wherein the expandable region expands in a non-spherical manner.

6. A device according to claim 1 wherein the expandable region expands in an essentially cylindrical manner.

7. A method for manipulating bone comprising the steps of deploying into bone an expandable structure having a wall material peripherally defining an interior space, the structure having a proximal and a distal end, the structure further having a first expandable region located near the distal end and a second expandable region located proximally of the first expandable region, the first and second expandable regions separated by a third region of the structure, the third region having a reduced cross-sectional area as compared to the cross-sectional areas of the first and second regions, and the first expandable region, the second expandable region, and the third expandable region further having, respectively, a first average wall thickness, a second average wall thickness, and a third average wall thickness, and the third average wall thickness being greater than either the first average wall thickness or the second average wall thickness, and expanding the device in bone to manipulate bone.

8. A method according to claim 7 wherein the wall material of the first expandable region substantially surrounds a first maximum cross-sectional area of the interior space, the wall material of the second expandable region substantially surrounds a second maximum cross-sectional area of the interior space, and the wall material of the third region substantially surrounds a minimum cross-sectional area of the interior space, the first and second maximum cross-sectional areas each being larger than the minimum cross-sectional area.

9. A method according to claim 7 wherein the wall material comprises polyurethane.

10. A method for compacting cancellous bone comprising the steps of deploying into bone a device having a wall made from a flexible material, the wall peripherally defining an interior space and including an expandable region, the expandable region having proximal and distal ends, the expandable region further having a first expanded section adjacent the distal end, a second expanded section located proximally of the first expanded section, and a third section located between the first and second expanded sections, wherein the average outer diameter of the third section is less than the average outer diameter of either of the first or second expanded sections, and the first expandable region, the second expandable region, and the third expandable region further having, respectively, a first average wall thickness, a second average wall thickness, and a third average wall thickness, and the third average wall thickness being greater than either the first average wall thickness or the second average wall thickness, and expanding the device inside bone to compact cancellous bone.

11. A method according to claim 10 wherein the expandable region expands in response to introduction of a flowable material into the interior space.

* * * * *